United States Patent
Stürzebecher et al.

(12)
(10) Patent No.: US 6,524,258 B1
(45) Date of Patent: Feb. 25, 2003

(54) METHOD FOR AN OBJECTIVE FREQUENCY-SPECIFIC DETERMINATION OF AN AUDIBLE THRESHOLD VALUE USING AN AMPLITUDE MODULATION FOLLOWING RESPONSE (AMFR)

(75) Inventors: Ekkehard Stürzebecher, Frankfurt am Main (DE); Mario Cebulla, Frankfurt am Main (DE); Matthias Baag, Blankenfelde (DE); Rainer Thie, Blankenfelde (DE)

(73) Assignee: Pilot Blankenfelde Medizinisch-Elektronische Geräte GmbH, Blankenfeld (DE)

(*) Notice: Subject to any disclaimer, the term of this patent is extended or adjusted under 35 U.S.C. 154(b) by 52 days.

(21) Appl. No.: 09/709,799

(22) Filed: Nov. 10, 2000

(30) Foreign Application Priority Data

Nov. 13, 1999 (DE) .......................... 199 54 666

(51) Int. Cl.⁷ ................................ A61B 5/00
(52) U.S. Cl. .................................... 600/559
(58) Field of Search ................ 600/559, 544, 600/378; 128/920; 73/585

(56) References Cited

U.S. PATENT DOCUMENTS

| | | | |
|---|---|---|---|
| 4,462,411 A | 7/1984 | Rickards | .................. 128/746 |
| 5,023,783 A | 6/1991 | Cohen et al. | .......... 364/413.02 |

FOREIGN PATENT DOCUMENTS

AT    WO 99/53838    4/1999

OTHER PUBLICATIONS

J. Acoust. Soc. Am. 90 (5), Nov. 1991—Lawrence T. Cohen—(A comparison of steady–state evoked potentials to modulated tones in a wake and sleeping humans).

J. Acoust. Soc. Am. 97 (5), Pt. 1, May 1995—Otavio G.Lins—(Auditory steady–state responses to tones amplitude–modulated at 80–110 Hz).

Geburtstagsgrüsse nach Freiburg i. Br.

*Primary Examiner*—Max F. Hindenburg
*Assistant Examiner*—Brian Szmal
(74) *Attorney, Agent, or Firm*—Norris Mclaughlin & Marcus, P.A.

(57) ABSTRACT

A method is described for and objective and frequency-specific determination of the audible threshold using an amplitude modulation following response (AMFR), for application in particular with infants and small children. According to the concept of the invention, instead of a single amplitude-modulated carrier, several carriers, preferably 3 or 5 carriers, having a frequency that is offset by a frequency difference $\Delta F$, preferably $\Delta F = F_{Mod}$ or $\Delta F = 2 F_{Mod}$, are used as a stimulus, wherein all carriers with the same modulation frequency $F_{Mod}$ are modulated with an amplitude swing between 30% and 100%, preferably 100%. In addition, one or several of the amplitude-modulated carriers, which for an odd number of carriers are preferably the carriers located between the outermost carriers, can be frequency-modulated, wherein a frequency swing between 0% and 30%, preferably 20%, is selected. With these preferred parameters, the frequency specificity of the measurement is not substantially limited by the spectral width of the stimulus.

17 Claims, 2 Drawing Sheets

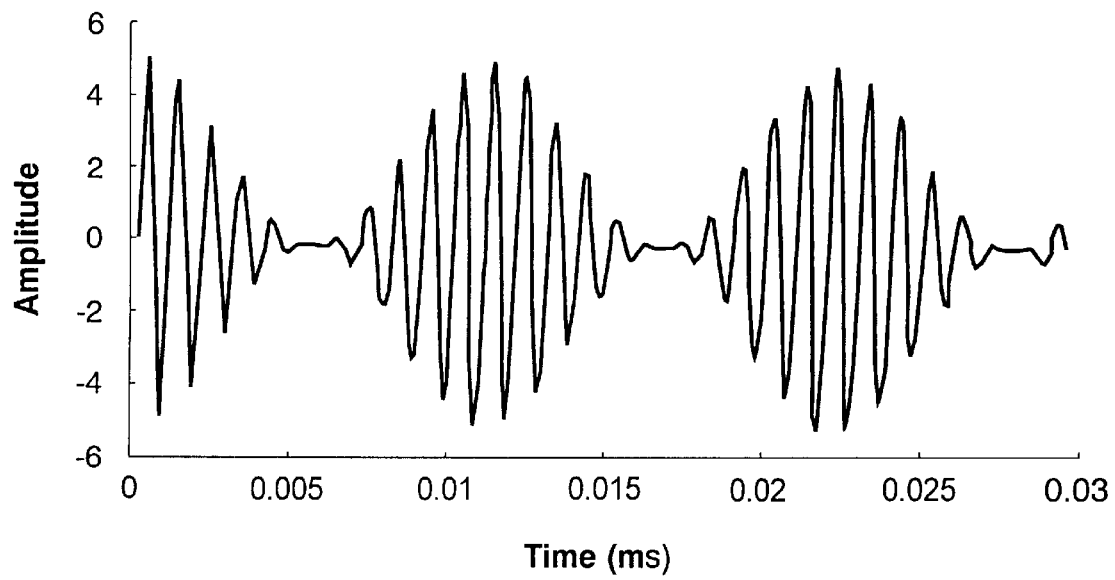
Figure 1.1
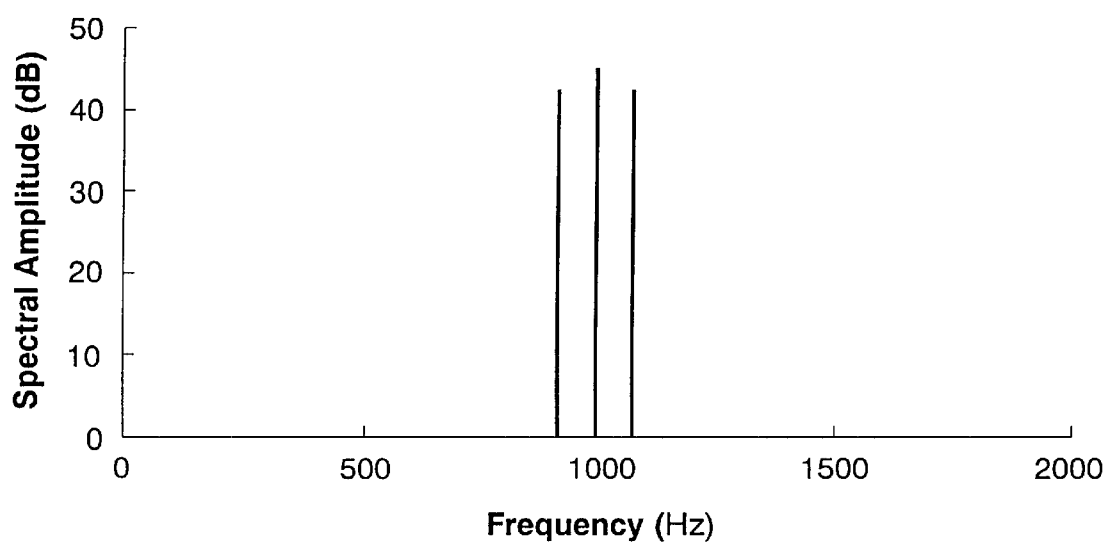
Figure 1.2

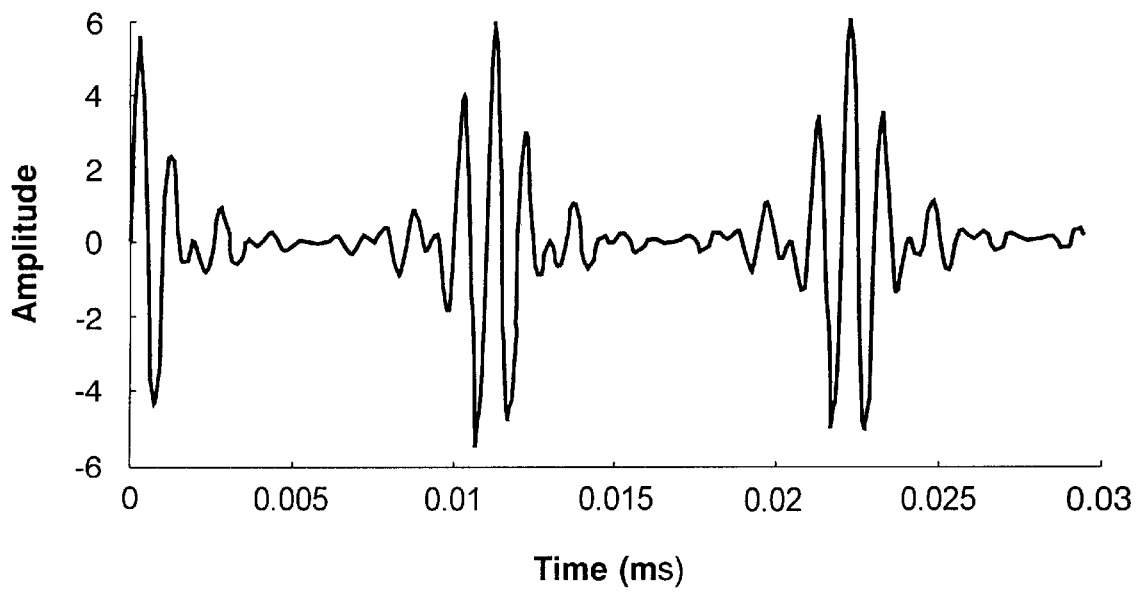
Figure 2.1
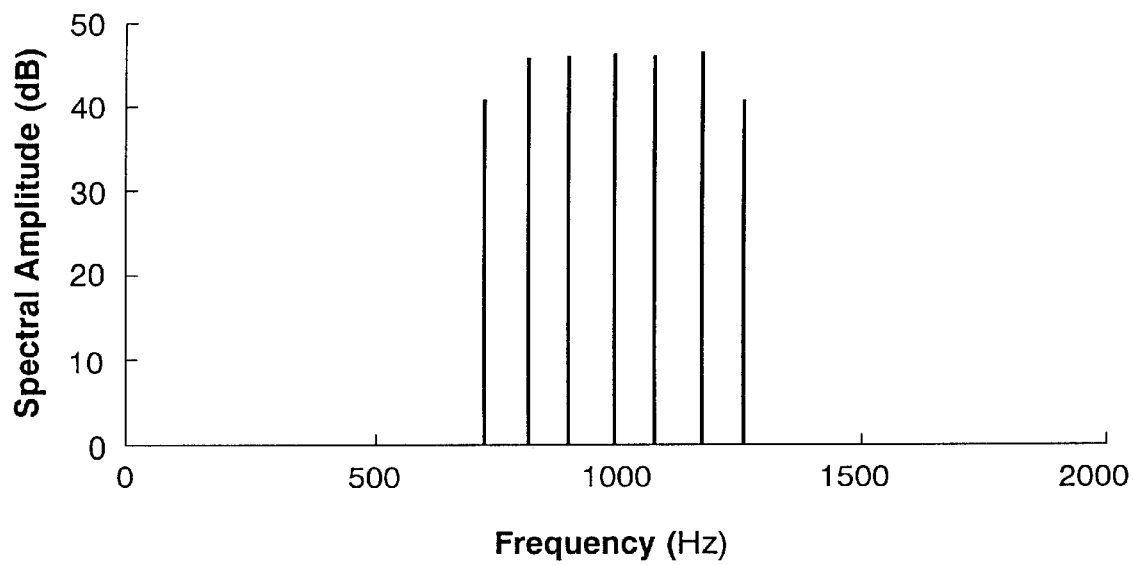
Figure 2.2

METHOD FOR AN OBJECTIVE FREQUENCY-SPECIFIC DETERMINATION OF AN AUDIBLE THRESHOLD VALUE USING AN AMPLITUDE MODULATION FOLLOWING RESPONSE (AMFR)

BACKGROUND OF THE INVENTION

1. Field of the Invention

The present invention relates to the field of a objective determination of the audible threshold, i.e., independent of the cooperation by the patient, by using Acoustically Evoked Potentials (AEP).

2. Description of the Related Art

The objective hearing test is used in particular with infants and small children since at that age the otherwise customary subjective audiometry which requires an active participation of the patient, is not yet possible.

It is known to automatically determine the hearing response with click stimuli, as disclosed in the patent DE 195 48 982.9 A1. A click stimulus only gives as a result the sum of the Early Acoustically Evoked Potentials (FAEP) in the frequency range of approximately 1000 Hz–8000 Hz. Hence, it is not possible to determine the audible threshold for specific frequencies.

Also known is the frequency-specific determination of the audible threshold based on sound pulse-evoked FAEP with additional notched-noise-masking (Stürzebecher E, Wagner H, Cebulla M, Heine S, Jerzynski P. Rationelle objektive Hörschwellenbestimmung mittels Tonpuls-BERA mit Notched-Noise-Maskierung {Rational objective determination of the audible threshold using sound pulse BERA with Notched-Noise masking}. Audiologische Akustik 1993; 32:164–176). With this method, only the measured data have so far been objective, whereas the registration (decision: response present/not present) has to be evaluated by an examiner. The problem of an objective evaluation is therefore not solved. An automatic control of the entire examination process is therefore not possible. Additional disadvantages are a long duration of the examination, possibly severe audible stress caused by the masking noise.

A method for determining the audible threshold using the amplitude modulation following response (AMFR) is known from Cohen LT, Richards FM, Clark GM. A comparison of steady-state evoked potentials to modulated tones in awake and sleeping humans. J. Acoust. Soc. Am. 1991; 90: 2467–2479, and Griffiths SK, Chambers RD. The amplitude modulation-following response as a audiometric tool. Ear Hear 1991; 12: 235–241.

AMFR is a so-called "steady-state response." AMFR results are obtained without applying short acoustic stimuli (sound pulses, clicks) in short sequence, as is otherwise customary. Instead, the stimulus is represented by a continuous amplitude-modulated tone. The frequency of the modulated tone is referred to as carrier frequency ($F_{Tr}$), the frequency of the modulation signal as modulation frequency ($F_{Mod}$). FIG. 1.1 shows the 1000 Hz stimulus signal in the time domain, FIG. 1.2 in the spectral domain. The hearing test is performed in the range $F_{Tr} \pm F_{Mod}$. The response is represented by a continuous sinusoidal signal with a frequency that corresponds to the modulation frequency.

The AMFR is evaluated in the spectral domain.

A hearing test using AMFR has the following advantages as compared to the usual hearing test using FAEP:

The response to the stimulus is frequency-specific without additional masking.

While the customarily used FAEP is characterized by a broad and very variablespectrum, AMFR is limited to a single spectral line. An objective statistic measurement of the AMFR is therefore much simpler than with the other AEPs.

Typically, an electrical stimulus artifact is captured together with the acoustic stimulation via headphones during an EEG derivation, which when using customary AEP cannot be safely segregated from the physiological response either in the time domain or in the frequency domain. With AMFR derivation, the carrier and the sidebands separated by the modulation frequency produce an electrical artifact. Since the response to a single spectral line that is not in the frequency range of the carrier is limited, the response and the stimulus artifact can be separated reliably without any problem.

A simultaneous test with several frequencies is possible (Lins OG, Picton TW. Auditory steady-state responses to multiple simultaneous stimuli. Electroenceph. Clin. Neurophysiol. 1995; 96: 420–432), thus making the examination shorter than with the notched-noise BERA.

The known solutions have the following disadvantages:

The amplitude of the response to the stimuli is in the nanovolt range, in other words, very small. The AMFR has always a superimposed noise (EEG). The signal-to-noise ratio (SNR) is also very small. This applies particularly in situations close to the audible threshold since the amplitude of the response decreases with decreasing stimulus level. In addition, the response amplitude has a relatively large scatter between individual patients. This causes a corresponding scatter for determining the response near the threshold. This scatter is too large for practical applications. To increase the response amplitude, Cohen et al. (1991) also amplitude-modulated a frequency-modulated carrier. However, the amplitude gain as compared to the simple amplitude modulation is insufficient. A commercial device for objectively determining the audible threshold based on AMFR is not known to this date.

SUMMARY OF THE INVENTION

It is an object of the invention to develop an objective frequency-specific hearing test procedure using the Amplitude Modulation Following Response (AMFR) that can be performed completely automatically and allows a reliable determination of the frequency-dependent audible threshold.

A solution of the object of the invention is recited in claim 1. Further embodiments of the invention are recited in the dependent claims. With the known simulation using an amplitude-modulated carrier, only a small range is activated on the basilar membrane of the inner ear corresponding to the small spectral width of the stimulus ($F_{Tr} \pm F_{Mod}$). The amplitude of the derived sum response is therefore small. A greater response amplitude can be expected if the spectral width of the stimulus is increased, while recognizing that the response still remains limited to exactly a single spectral line.

According to the concept of the invention, instead of a single amplitude-modulated carrier, several carriers, preferably 3 or 5 carriers, having a frequency that is offset by a frequency difference $\Delta F$, preferably $\Delta F = F_{Mod}$ or $\Delta F = 2 F_{Mod}$, are used as a stimulus, wherein all carriers with the same modulation frequency $F_{Mod}$ are modulated with an amplitude swing between 30% and 100%, preferably 100%. In addition, one or several of the amplitude-modulated carriers, which for an odd number of carriers are preferably the carriers located between the outermost carriers, can be frequency-modulated, wherein a frequency swing between 0% and 30%, preferably 20%, is selected. With these preferred parameters, the frequency specificity of the measurement is not substantially limited by the spectral width of the stimulus.

Unlike conventional methods, which decide "AMFR present/not present" in a single statistical test, it is proposed to subject the data to several, preferably four, statistical test methods and to assume that an AMFR is present as soon as at least two of the test indicate significance. Determination of the audible threshold can either be performed completely automatic or can be controlled by the examiner.

If the audible threshold is determined by an examiner, then it is proposed to link the PC interfaces which a separate in conventional solutions, for selecting the stimulus (frequency, stimulus level) and displaying the result (audiogram) in the following fashion: a respective audiogram form (DIN standard) is displayed on the PC monitor for the right and left ear, or alternatively can be switched between the right and left ear. An acoustic stimulus with a specified frequency and a specified level is selected by clicking with the mouse on the intersection of the vertical scan line for the frequency marked on the abscissa with the horizontal scan line for the stimulus marked on the ordinate. Alternatively, the intersection can be selected by the arrow keys on the PC keyboard. When using several test frequencies simultaneously for the hearing test (Lins and Picton 1995), a second and, optionally, a third stimulus parameter pair is preselected in the same way. After the start of the measurement and the statistical test, the result (a response to the stimulus is present/not present) is marked on the audiogram form at the intersection of the test frequency and the stimulus level so that the presence or absence of a response to the selected stimulus parameters can be detected.

Applying the solution of the invention has following advantages:

The width of the stimulus spectrum can be preset exactly

The spectrum is almost a rectangle, i.e., all the spectral lines forming to spectrum have almost the same amplitude The response is limited to only the modulation frequency On average, the SNR characterizing the response amplitude is greater by a factor 2 than for a conventional simulation using a single amplitude-modulated carrier and also greater than the response obtained with an additional frequency modulation of the single amplitude-modulated carrier. The scatter in the difference between the subjectively and objectively determined audible threshold occurring in the conventional stimulation is thus significantly reduced, so that the objective hearing test method can be used in practice By using known statistical test methods with AMFR detection, a fully automatic objective frequency-specific hearing test can be implemented The proposed solution has a lower probability for a fault-positive test result than a process where the decision "AMFR present/not present" is based on a single test, or where four difference statistical test methods (e.g.) are applied and the presence of an AMFR is postulated as soon as two of the tests indicate a significance When applying the stimulus configuration of the invention, the simultaneous hearing test proposed by Lins & Picton (1995) using several different test frequencies can also be implemented without limitation A different spectral width of the stimulus can be set that is tuned to the frequency range to be tested By linking the selection of the stimulus parameters with the display of the results, there is no longer a need to switch between displaying the result (determining which stimulus parameter is to be selected next) and the menu for selecting the stimulus parameters. This prevents arrow's in the selection of the stimulus parameters, a particular for a simultaneous hearing test with several frequencies With the proposed linkage of selection of stimulus parameters with the display of the result, both the stimulus parameter frequency and the stimulus level are selected with a single mouse click. The graphic display of the result indicates immediately which stimulus parameters should be selected for the next step in the examination.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

In the drawings, wherein like reference numerals delineate similar elements throughout the several views:

FIG. 1.1 shows a 1000 Hz stimulus signal in the time domain;

FIG. 1.2 shows the spectrum of the temporal function shown in FIG. 1.1;

FIG. 2.1 shows the temporal function of the acoustic stimulus as a superposition of three amplitude-modulated carriers having a separation of 2 $F_{Mod}$; and FIG. 2.2 shows the spectrum of the temporal function shown in FIG. 2.1.

DETAILED DESCRIPTION OF THE PRESENTLY PREFERRED EMBODIMENTS

For a small child with a suspected severe audible dysfunction, the frequency-specific audible threshold should be determined using AMFR, since the results obtained using conventional subjective methods are not sufficiently accurate for this age group. These results are hence unsuitable to provide a child with a hearing aid and possibly a cochlear implant.

The examination is performed during the natural sleep or while sedated. The hearing test is carried out at frequencies of 250 Hz, 500 Hz, 1000 Hz, 2000 Hertz and 4000 Hz. The composition of the acoustic stimuli will now be described with reference to the stimulus for the 1000 Hz frequency range:

The modulation frequency is $F_{Mod}$=89.84375 Hz. The acoustic stimulus is comprised of three carriers whose respective frequency is offset by the frequency difference $\Delta F = 2_{Fmod}$:

$F_{Tr\ 0}$=988.28 Hz $F_{Tr\ 1}=F_{Tr\ 0}+2\ F_{Mod}$=1167.9675 Hz $F_{Tr\ 2}=F_{Tr\ 0}-2\ F_{Mod}$=808.5925 Hz

The center carrier is frequency- and amplitude-modulated, the frequency swing is 20%, the amplitude swing 100%. The frequency and amplitude modulation have the same phase. The non-integer frequencies are the result of the requirement that the period duration of the modulation frequency is an integer multiple of the period duration of the carrier frequencies. The second requirement is that the length of an waveform epoch that has been transformed by a Fourier transformation (FT) of the derived EEG is an integer multiple of the period duration of the modulation signal.

The spectrum of the stimulus is illustrated in FIG. 2.1. A detail of the temporal function of the stimulus without frequency modulation of the center carrier is illustrated in FIG. 2.2.

Before the examination begins, the stimulation signal is computed in the control PC over the lengthy of a waveform epoch and stored in memory. The computed stimulus segment includes only integer multiples of the three carrier frequencies and of the modulation frequency. The memory is read out cyclically during the acoustic stimulation. The produced continuous signal is D/A converted, amplified and transmitted with the desired level (dBnHL) to the ear of the patient via headphones.

During the acoustic stimulation, the EEG is conducted away from the scalp by adhesive electrodes. The electrode is placed vertex/ipsilateral mastoid, ground: forehead. The EEG is amplified and A/D converted. The clock frequency for the D/A converter and the A/D conversion has to be synchronized. Otherwise, it could not be guaranteed that a digitized waveform epoch of the amplified EEG contains only integer multiples of the modulation frequency and the carrier frequency. This would cause sidebands to be introduced in the useful signal and the stimulus artifacts due to "incomplete" periods in the FT.

In the description below, it will be assumed that the clock frequencies of the D/A converter and the A/D converter have an identical value of 16 kHz. The digitized EEG is continuously stored during the stimulation.

A waveform epoch is represented by 4096 sampled values and has a length of 0.256 seconds. Parallel to the acoustic stimulus and data capture, EEG segments with a length of 8 waveform epochs (2.048 seconds), in the following also referred to as sweeps, are transformed into the spectral regime using FT. The spectrum computed for each sweep is stored. The frequency resolution of the spectrum is 0.48828125 Hz (1/2.048 seconds).

In the aforedescribed exemplary application, determination of the audible threshold is controlled by an examiner. The process will be described with reference to the determination of the audible threshold of the right ear at 1000 Hz. The start stimulus level is assumed to be 60 dBnHL. The stimulus parameters are selected by clicking with the mouse on the intersection 1000 Hz/60 dBnHL in the audiogram form on the display. The examination starts by pressing the ENTER key. As soon as the spectra of 20 sweeps are captured, the first statistic testing is performed using four test methods. A new test is performed after the number of samples is increased by five sweeps. As long as the test result is not significant for at least two of the four tests, the number of samples is continuously augmented until a response is detected or until a predetermined maximum number of samples (e.g., 50 sweeps) are reached. It will be assumed that no answer is recorded at 1000 Hz/60 dBnHL even after 50 sweeps. This is marked accordingly on the audiogram form on the monitor, for example by placing a gray circle at the intersection 1000 Hz/60 dBnHL. The examiner then increases the stimulus level to, for example, 80 dBnHL by clicking with the mouse on the intersection 1000 Hz/80 dBnHL. It shall now be assumed that a response is detected at 80 dBnHL. This is marked by placing a red circle at the intersection 1000 Hz/80 dBnHL. The examiner now selects a stimulus level of 70 dBnHL. It will be assumed that no response is detected at this stimulus level. The intersection 1000 Hz/70 dBnHL will be marked in the audiogram form with a gray circle. The audible threshold will be assumed to be at 80 dB.

The examination at the frequencies 250 Hz, 500 Hz, 2000 Hz and 4000 Hz is performed in the same manner, optionally simultaneously at two or three frequencies, with a separation of preferably 2 octaves. If a response is detected at one frequency for several stimulus levels, then only the intersection for the lowest stimulus level is marked by a red circle, whereas the others intersections are marked, for example, by a pink circle. The intersections at the five frequencies are marked with red circles that are connected by a continuous red line (=audible threshold curve).

Optionally, the audible threshold can be determined individually for each frequency or according to the proposal by Lins and Picton (1995) simultaneously for several frequencies. The test can be performed in steps of 5 dB which, however, takes much longer since an additional examination is required at each frequency, in the present example at 1000 Hz/75 dBnHL.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A method for an objective frequency-specific determination of an audible threshold-value using an amplitude modulation following response (AMFR), comprising the steps of:
   amplitude modulating a plurality of carriers as stimuli for acoustic stimulation, the plural carriers having carrier frequencies mutually offset by a frequency difference;
   employing a plurality of statistical test methods for objectively detecting the AMFR; and
   detecting the presence of an AMFR if at least two of the statistical test methods yield a significant result.

2. The method according to claim 1, wherein the frequency difference is equal to the modulation frequency.

3. The method according to claim 1, wherein the frequency difference is twice the modulation frequency.

4. The method according to claim 2, wherein the stimuli is three or five carriers, and wherein all carriers with the same modulation frequency are modulated with an amplitude swing between approximately 30% and approximately 100%.

5. The method according to claim 3, wherein the stimuli is three or five carriers, and wherein all carriers with the same modulation frequency are modulated with an amplitude swing between approximately 30% and approximately 100%.

6. The method according to claim 4, wherein there is an odd number of carriers of which two are outermost carriers with at least one carrier disposed therebetween, the at least one carrier located between the two outermost carriers being frequency-and amplitude modulated.

7. The method according to claim 6, wherein a frequency swing between 0% and approximately 30% is selected.

8. The method according to claim 5, wherein the amplitude modulating step further comprises using stimuli with different bandwidths for determining an audible threshold for low, intermediate and high audio frequencies, wherein the bandwidth of the stimulus is changed by changing the number of the carriers and/or the frequency difference between the carrier frequencies.

9. The method according to claim 8, wherein four different statistical methods are used.

10. The method according to claim 9, wherein the employing step comprises determining an audible threshold curve by the examiner or automatically using a control algorithm.

11. The method according to claim 10, wherein the audible threshold is determined using the control algorithm, and the employing step further comprises receiving an initial stimulus level preset by the examiner for only a single frequency and a beginning stimulus level for the remaining frequencies being selected adaptively by the control algorithm based on previously determined audible thresholds.

12. The method according to claim 11, wherein the audible threshold is determined by the examiner, and the employing step further comprises selecting as stimulus parameters a desired test frequency and a test stimulus level representing intersections on a displayed audiogram form.

13. The method according to claim 12, further comprising the step of identifying the result on the audiogram form.

14. The method according to claim 1, wherein the method is used for testing hearing in infants or small children.

15. The method according to claim 6, wherein for an odd number of carriers, the at least one carriers frequency modulated is located between the outermost carriers.

16. The method according to claim 11, wherein the control algorithm selects the beginning stimulus level for the remaining frequencies based on the audible threshold of an adjacent frequency.

17. The method according to claim 13, wherein at each frequency the intersection for the lowest stimulus level at which a response has been detected is marked with audiometry labels and marked points of intersection at the different frequencies are connected by a continuous line.

* * * * *

UNITED STATES PATENT AND TRADEMARK OFFICE
CERTIFICATE OF CORRECTION

PATENT NO.     : 6,524,258 B1  
DATED          : February 25, 2003  
INVENTOR(S)    : Ekkehard Stuerzebecher et al.

It is certified that error appears in the above-identified patent and that said Letters Patent is hereby corrected as shown below:

<u>Title page,</u>
Item [56], FOREIGN PATENT DOCUMENT, was incorrectly cited as
"AT   WO 99/53838   4/1999" it should read -- AU   WO 99/53839   4/1999 --

OTHER PUBLICATION, incorrectly reads "Geburtstagsgruesse nach Freiburg i. Br." it should read -- Geburtstagsgruesse nach Freiburg I. Br., "Rationelle objektive Hoerschwellen-bestimmung mittels Tonpuls-BERA mit Notched-Noise-Maskierung," Audiologische Akustik, (1993) 164-177 --

Signed and Sealed this

Twenty-fourth Day of June, 2003

JAMES E. ROGAN  
*Director of the United States Patent and Trademark Office*

UNITED STATES PATENT AND TRADEMARK OFFICE
CERTIFICATE OF CORRECTION

PATENT NO.    : 6,524,258 B1
DATED         : February 25, 2003
INVENTOR(S)   : Ekkehard Stürzebecher et al.

It is certified that error appears in the above-identified patent and that said Letters Patent is hereby corrected as shown below:

<u>Title page,</u>
Item [56], OTHER PUBLICATIONS, incorrectly reads "Geburtstagsgruesse nach Freiburg i. Br." (as deleted by Certificate of Correction issued June 24, 2003) should be reinstated.

Signed and Sealed this

Twelfth Day of August, 2003

JAMES E. ROGAN
*Director of the United States Patent and Trademark Office*